US012575789B2

(12) United States Patent
Gabriel et al.

(10) Patent No.: US 12,575,789 B2
(45) Date of Patent: Mar. 17, 2026

(54) FLUID SENSING DEVICES INCLUDING FLUID ABSORPTION AND DISTRIBUTION LAYER

(71) Applicant: 3M INNOVATIVE PROPERTIES COMPANY, St. Paul, MN (US)

(72) Inventors: Nicholas T. Gabriel, Grand Rapidsa, MN (US); Manjiri T. Kshirsagar, Woodbury, MN (US); Ronald D. Jesme, Plymouth, MN (US); Justin Tungjunyatham, Roseville, MN (US); Hamid R. Mortazavi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1289 days.

(21) Appl. No.: 17/309,638

(22) PCT Filed: Dec. 18, 2019

(86) PCT No.: PCT/IB2019/061025
§ 371 (c)(1),
(2) Date: Jun. 11, 2021

(87) PCT Pub. No.: WO2020/128903
PCT Pub. Date: Jun. 25, 2020

(65) Prior Publication Data
US 2022/0022811 A1      Jan. 27, 2022
Related U.S. Application Data

(60) Provisional application No. 62/783,609, filed on Dec. 21, 2018.

(51) Int. Cl.
*A61B 5/00* (2006.01)
*G01N 1/44* (2006.01)
(Continued)

(52) U.S. Cl.
CPC ............. *A61B 5/4875* (2013.01); *G01N 1/44* (2013.01); *G01N 25/18* (2013.01); *G01N 25/58* (2013.01); *H01Q 7/00* (2013.01)

(58) Field of Classification Search
CPC ..... A61B 5/4875; A61B 5/0002; A61B 5/443; G01N 1/44; G01N 25/18; G01N 25/58; G01N 25/56; H01Q 7/00; G08C 17/02
See application file for complete search history.

(56) References Cited

U.S. PATENT DOCUMENTS

| 2008/0051745 | A1 | 2/2008 | Long |
| 2013/0158492 | A1 | 6/2013 | Song |
| | | (Continued) | |

FOREIGN PATENT DOCUMENTS

| CA | 2869469 | 10/2013 |
| CN | 1839776 | 10/2006 |
| | (Continued) | |

OTHER PUBLICATIONS

Wood, Errol; Jul. 2017; https://www.woolwise.com/wp-content/uploads/2017/07/Wool-482-582-08-T-23.pdf (Year: 2017).*
(Continued)

Primary Examiner — Abid A Mustansir
(74) Attorney, Agent, or Firm — Sriram Srinivasan; Yufeng Dong

(57) ABSTRACT

Fluid sensing devices including a layer of fluid absorption and distribution material are provided. The layer includes a porous fibrous nonwoven matrix for absorbing fluid from the object to the first major surface of the layer and laterally distributing the absorbed fluid throughout the layer and to a second major surface of the layer opposite the first major surface. Hydration sensors are disposed on the second major surface of the layer to measure a hydration level.

17 Claims, 10 Drawing Sheets

(51) Int. Cl.
  *G01N 25/18*   (2006.01)
  *G01N 25/58*   (2006.01)
  *H01Q 7/00*   (2006.01)

(56)            References Cited

U.S. PATENT DOCUMENTS

| | | | |
|---|---|---|---|
| 2016/0029957 | A1 | 2/2016 | Faybishenko |
| 2017/0337461 | A1* | 11/2017 | Jesme ........................ G01J 5/02 |
| 2018/0144227 | A1 | 5/2018 | Jesme |

FOREIGN PATENT DOCUMENTS

| | | |
|---|---|---|
| KR | 10-2018-002231 | 1/2018 |
| WO | WO 2010-017360 | 2/2011 |
| WO | WO 2013-134522 | 9/2013 |
| WO | 2015094938 A1 | 6/2015 |
| WO | WO 2016-073344 | 5/2016 |
| WO | WO 2017-192429 | 11/2017 |

OTHER PUBLICATIONS

International Search report for PCT International Application No. PCT/IB2019/061025 mailed on Apr. 10, 2020, 3 pages.

\* cited by examiner

FLUID SENSING DEVICES INCLUDING FLUID ABSORPTION AND DISTRIBUTION LAYER

CROSS REFERENCE TO RELATED APPLICATIONS

This application is a national stage filing under 35 U.S.C. 371 of PCT/IB2019/061025, filed Dec. 18, 2019, which claims the benefit of U.S. Application No. 62/783,609, filed Dec. 21, 2018, the disclosure of which is incorporated by reference in its/their entirety herein.

TECHNICAL FIELD

The present disclosure relates to fluid sensing devices, and methods of making and using the sensing devices.

BACKGROUND

Portable electronic devices including fluid sensing devices have been widely used.

SUMMARY

The present disclosure provides fluid sensing devices based on heating a local region of a fluid absorption and distribution layer and measuring its thermal response. An increase in thermal conductivity and thermal diffusivity of that region when it absorbs fluid can be used to determine the quantity of fluid absorbed. There is a desire to improve uniform distribution of fluid throughout the fluid absorption and distribution layer.

In one aspect, the present disclosure describes a fluid sensing device including one or more hydration sensors, and a layer of fluid absorption and distribution material. The one or more hydration sensors is disposed on the layer of fluid absorption and distribution material, and the layer of fluid absorption and distribution material includes a porous fibrous nonwoven matrix.

In another aspect, the present disclosure describes a method for quantitative fluid sensing. The method includes providing a layer of fluid absorption and distribution material having a first major surface in fluid communication with an object; absorbing fluid from the object to the first major surface of the layer and laterally distributing the absorbed fluid throughout the layer and to a second major surface of the layer opposite the first major surface; and providing one or more hydration sensors disposed on the second major surface of the layer to measure a hydration level thereof. The layer of fluid absorption and distribution material includes a porous fibrous nonwoven matrix.

Various unexpected results and advantages are obtained in exemplary embodiments of the disclosure. One such advantage of exemplary embodiments of the present disclosure is that a layer of fluid absorption and distribution material described herein can absorb fluid from an object to a first major surface thereof and uniformly distribute the absorbed fluid laterally throughout the layer and to an opposite second major surface. With such a uniform fluid distribution, a sensing element with a relatively small footprint provided on the second major surface can measure a hydration level at a local area which is representative to the whole layer.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which.

Figure 1A:
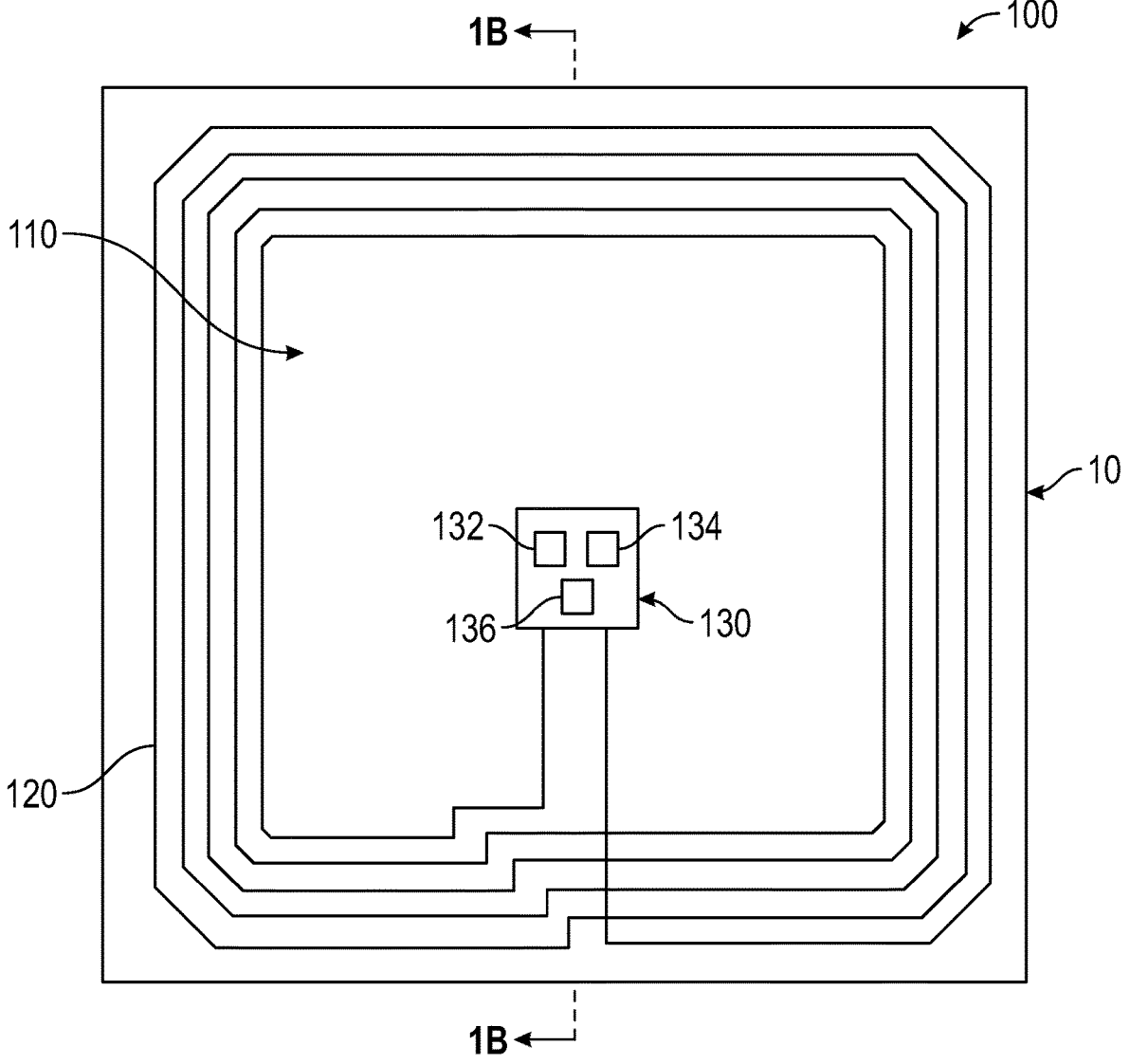
FIG. 1A illustrates a schematic top view of a wireless fluid sensing device including an antenna, according to one embodiment.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

Figure 1B:
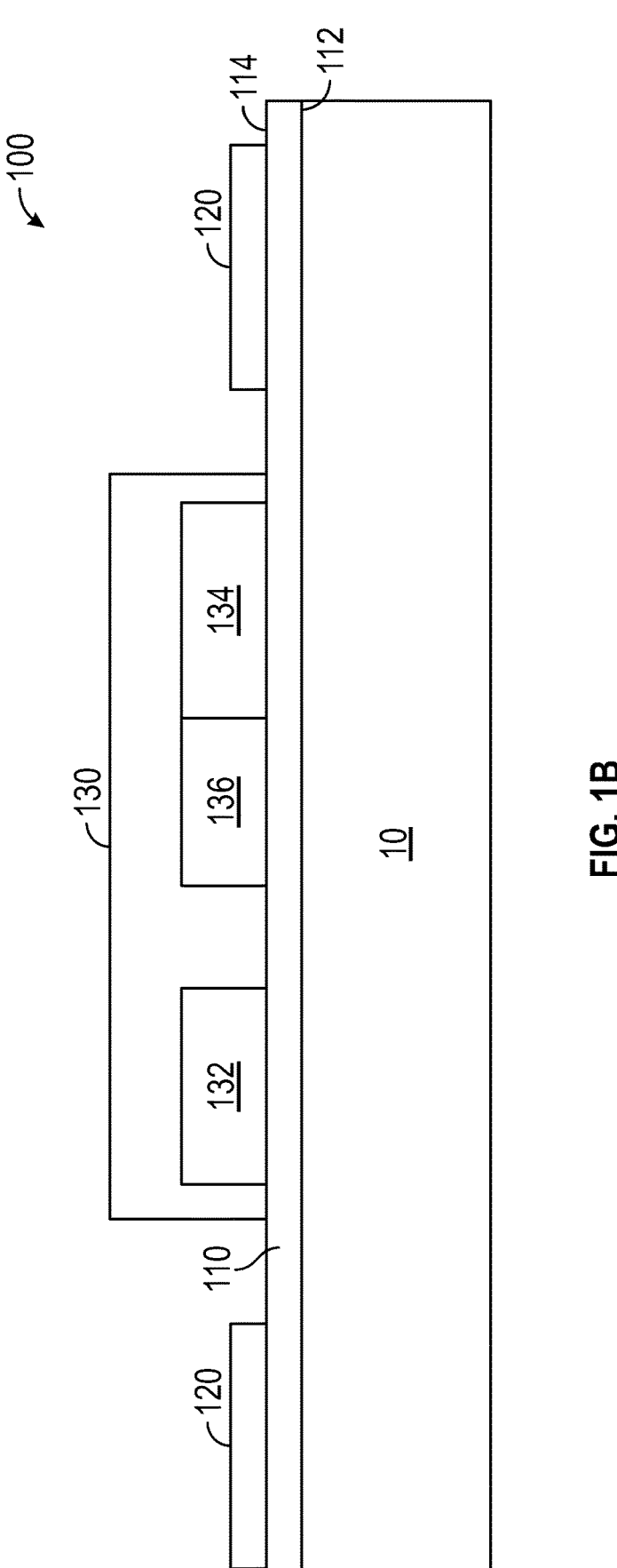
FIG. 1B illustrates a cross-sectional view of the wireless sensing device of FIG. 1A, according to one embodiment.

FIGS. 1A-B illustrate a wireless fluid sensing device 100, according to some embodiments. The wireless fluid sensing device 100 or referred to as a radio-frequency (RF) sensor tag, includes a substrate 110, an antenna 120, and a sensing circuit 130 electronically coupled to the antenna 120. The substrate 110 has a first major surface 112 and a second major surface 114 opposite to the first major surface 112. The antenna 120 is disposed on a peripheral portion of the major surface 114 or 112 of the substrate 110. The sensing circuit 130 is disposed on the second major surface 114 and includes an RF component 132 electrically coupled to the antenna 120. Exemplary sensing circuits are described in WO 2016/073344 (Jesme et al.), which is incorporated herein by reference.

The substrate 110 can be flexible or rigid. In some embodiments, the substrate 110 can be stretchable. In some embodiments, the substrate 110 can include a polymeric film. In some embodiments, the substrate 110 may include polyurethane. Suitable polymer films may include, for example, elastomeric polyurethane, co-polyester, polyether block amide, polyester, polyethylene, polyethylene naphthalate, silicones such as polydimethylsiloxane (PDMS), flexible epoxy, polyimide, polysulfide, fluoropolymer, etc. It is to be understood that the substrate 110 can made of any suitable materials for flex circuits such as, for example, any suitable materials for bandages, any films suitable for on-skin wear, etc.

The antenna 120 can have any suitable configurations designed for near-field coupling with an RF reader. The antenna 120 can be disposed on one or both sides of a substrate. In some embodiments, the antenna 120 can be a coil antenna. In some cases, the antenna 120 can have a spiral form. In some implementations, the antenna 120 can include one or more substantially concentric electrically conductive loops. In some configurations, the antenna can have a length between first and second ends, the length being less than, for example, about 2 meters. A coil antenna can have an inductance based on its geometry that produces a resonance with the capacitance of the electronically connected components, generally referred to as RF components, for enhanced induced voltage for a given magnetic field strength near the frequency of the RF reader.

When the wireless sensing device 100 is disposed proximate to an object (e.g., a skin of person) to measure, for example, a hydration level of the object, the sensing circuit 130 is positioned proximate to the object to measure properties of the object.

In the depicted embodiment of FIGS. 1A-B, the sensing circuit 130 includes the RF component 132 electrically coupled to the antenna 120. In some cases, the RF component 132 can perform modulation and demodulation according to the standards, ISO 14443A, ISO 15693, or other standard or proprietary communication protocols. The sensing circuit 130 further includes a heating element 134 and a sensing element 136 thermally coupled to the heating element 134 and configured to generate a sensor signal (e.g., sensing a temperature of the heating element 134). The RF component 132 can be functionally connected to the sensing element to receive the sensor signal and communicate the sensor signal with an external device via the antenna 120.

In some implementations, the RF component 132, which may include components of a transceiver and/or a control circuit, may be configured to contain a tunable or switchable capacitance to produce the at least two values of capacitance (i.e., the first capacitance, the second capacitance), or may contain circuitry for controlling an external variable capacitance, or may contain circuitry to allow one or more external capacitance elements to be switched in or out of the circuit.

In some embodiments, the heating element 134 and the sensing element 136 can be components of an integrated circuit. In some embodiments, the sensing element 136 may be a thermal sensor that detects measurable changes in an electrical property, an optical property, an acoustic property, or the like, in response to temperature changes.

In some embodiments, the sensing circuit 130 can be a hydration sensor configured to measure a hydration level of an object when the hydration sensor is disposed proximate to the object. The sensing circuit 130 can include one or more components including, for example, a transceiver, control circuit, an energy harvesting device, an energy storage device, thermal source, a sensor, etc. It is to be understood that the sensing circuit 130 can be any suitable types of sensors for sensing physical or chemical properties of an object to be measured.

In some embodiments, one or more of the antenna 120 and the sensing circuit 130 may be components of a radio frequency identification (RFID) tag. RFID tags on flexible and/or stretchable substrates are described in more details in U.S. Patent Application No. 62/031,581, entitled "RFID Tag on Stretchable Substrate" and filed on Jul. 31, 2014, and U.S. Patent Application No. 62/031,603, entitled "RFID Tag on Flexible Substrate" and filed on Jul. 31, 2014, the entirety of which are incorporated herein by reference.

Figure 1C:
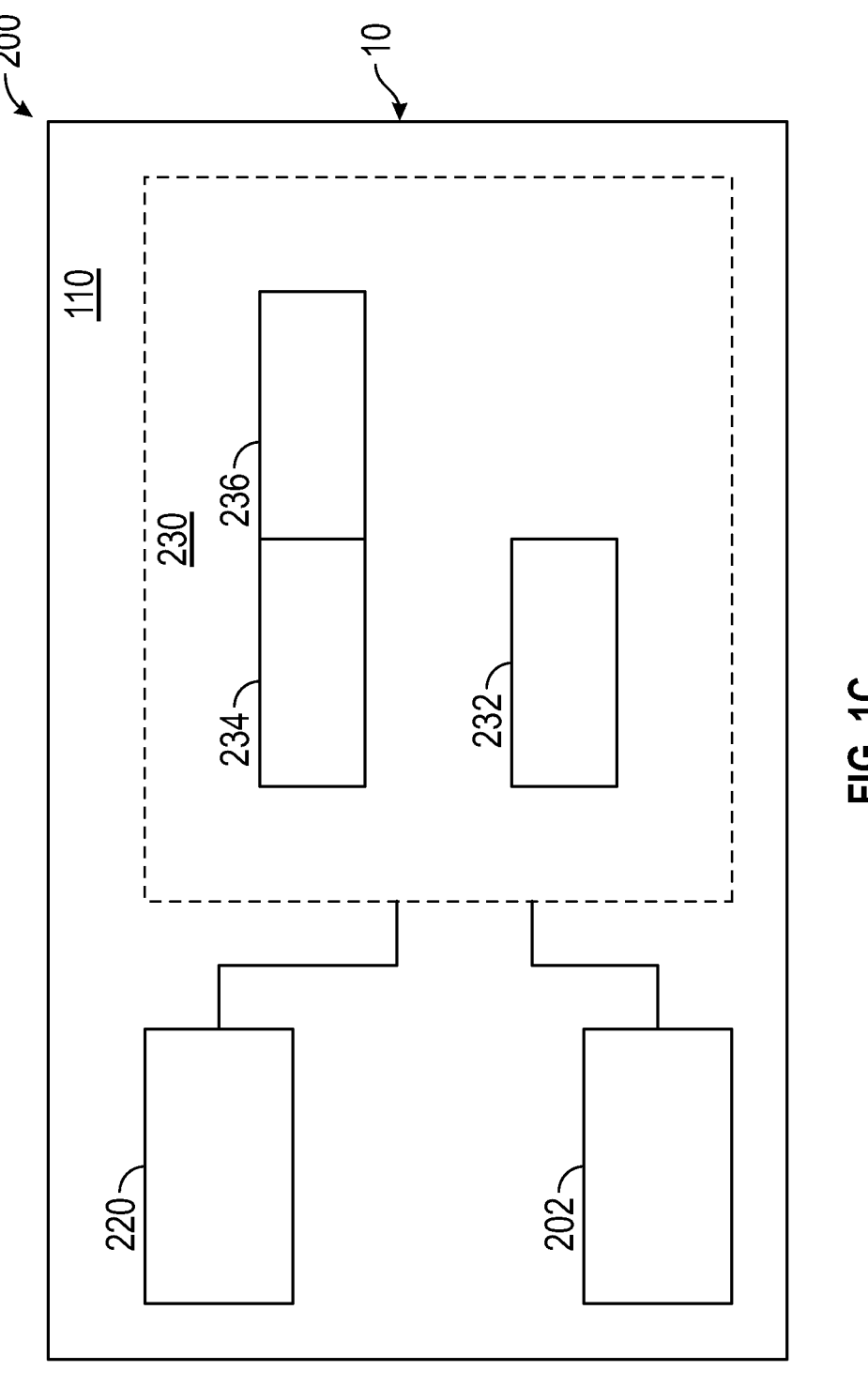
FIG. 1C illustrates a schematic top view of an active fluid sensing device, according to another embodiment.
Figure 1D:
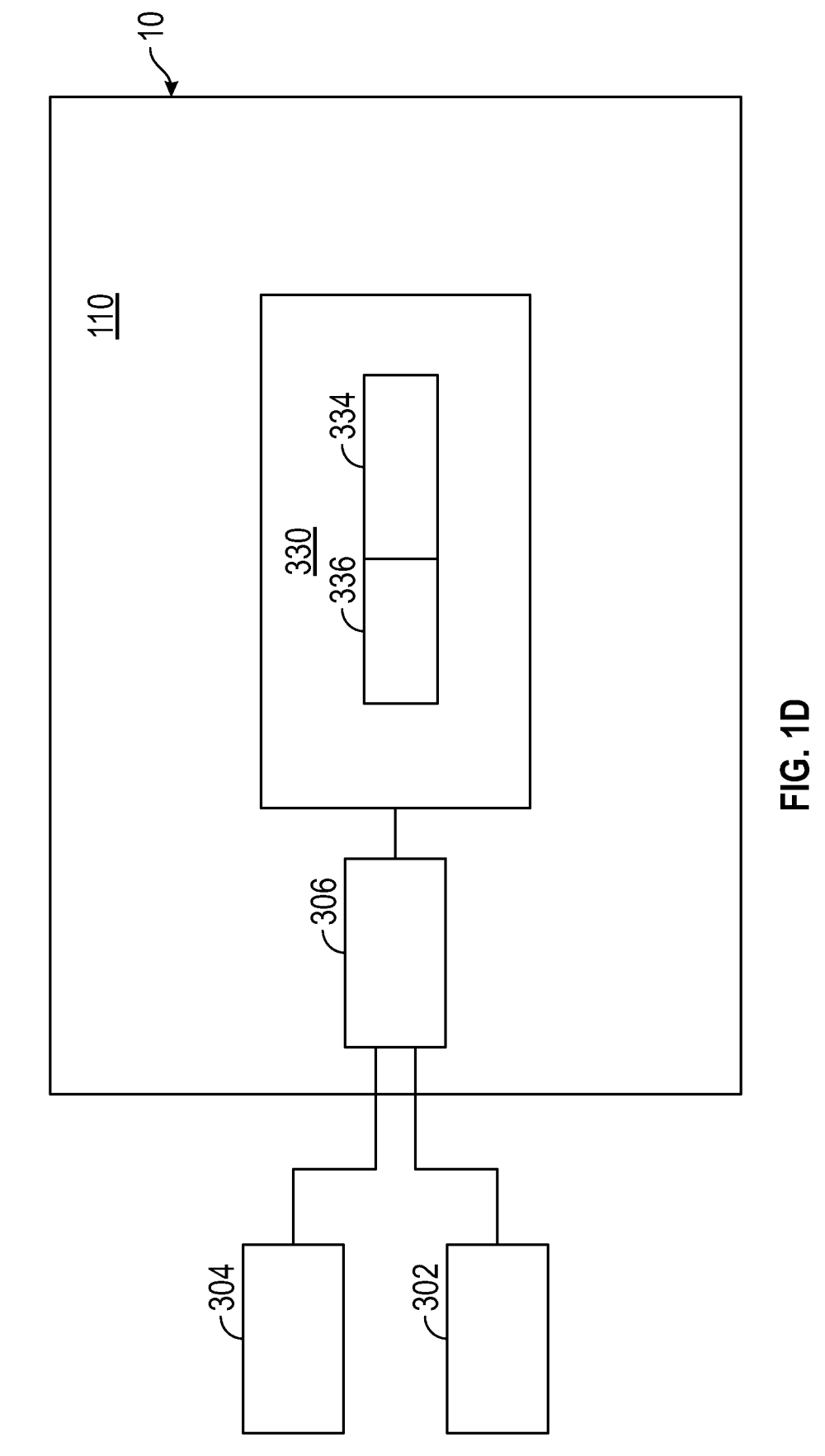
FIG. 1D illustrates a schematic top view of an active fluid sensing device, according to another embodiment.

While FIGS. 1A-B illustrate one embodiment of a passive wireless fluid sensing device, a fluid sensing device described herein can have other suitable configurations. For example, as shown in FIG. 1C, an active wireless fluid sensing device 200 includes a hydration sensing circuit 230 functionally connected to an antenna 220, and a power source 202 is configured to provide electrical power to the device 200. Similar to the sensing circuit 130 of FIGS. 1A-B, the hydration sensing circuit 230 includes a heating element 234 and a sensing element 236 thermally coupled to the heating element 234 and configured to generate a sensor signal (e.g., sensing a temperature of the heating element 134). The hydration sensing circuit 230 further includes an RF component 232 electrically coupled to the antenna 220. As shown in FIG. 1D, an active wired fluid sensing device 300 includes a hydration sensing circuit 330 functionally connected to a controller 304 via a connector 306, and a power source 302 is configured to provide electrical power to the device 300. Hydration sensing circuit 330 includes a heating element 334 and a sensing element 336 thermally coupled to the heating element 334 and configured to generate a sensor signal (e.g., sensing a temperature of the heating element 334). The hydration sensing circuit 330 may not require an RF component.

In the various embodiments illustrated, when a fluid sensing circuit (e.g., 130, 230, or 330) is thermally coupled to a target area, the sensing circuit 130 can sense a time variation of the target area temperature, and transmit the sensed time variation of the temperature. A processor can be provided to receive the sensor signal and determine a hydration indicator indicative of hydration level based on the sensed time variation of the target area temperature.

In the depicted embodiments of FIGS. 1A-D, the various fluid sensing device 100, 200 and 300 each include a fluid absorption and distribution layer 10 that serves as fluid absorption and distribution media to absorb liquid, such as sweat, wound exudate, condensate, perspiration, oil, etc., and to uniformly distribute the absorbed liquid throughout the layer 10. The layer 10 includes a porous fibrous non-woven matrix for absorbing fluid from the object to a first major surface 12 of the layer 14 and laterally distributing the absorbed fluid throughout the layer and to a second major surface 14 of the layer opposite the first major surface 12.

A thermal heating element (e.g., 134, 234, or 334) is in thermal contact with a target area of the fluid absorption and distribution layer 10 to provide heat to that local area. In some cases, the thermal heating element can be disposed proximate to each other and form thermal contact. In other cases, the thermal heating element can be in physical direct contact with the target area. In some cases, the thermal heating element is disposed on or at least partially in the absorbed liquid along the layer 10.

A sensing element (e.g., 136, 236, or 336) is thermally coupled to the thermal heating element to measure the thermal response of that target area which may depend on the concentration or properties of absorbed fluid in the target area. Local fluid concentration at a target area can be measured by introducing, via a heating element, a known amount of heat into the target area and measuring the resulting temperature change with time. In some cases, the local fluid concentration can be inversely proportional to the induced change in temperature ($\Delta T$) per unit of input power (heat). Detailed discussion of such a working principle can be found in WO2016073344.

In general, the extent of the local region affecting the thermal response includes a vertical extent and a lateral extent. The vertical extent (i.e. thickness) of the local region affecting the thermal response can be designed to be similar to or less than the thickness of the fluid absorption and distribution layer 10, such that the measurement of its thermal response primarily indicates the state of the fluid absorption and distribution layer 10. The vertical extent may be referred to as the probing depth of the measurement, defined primarily by the duration of time of heating and the effective thermal diffusivity of the fluid absorption and distribution layer 10. Thermal diffusivity, a derived material property, is the ratio of thermal conductivity to the product of density and specific heat capacity. The fluid absorption and distribution layer 10 is an effective medium containing multiple materials, thus it has effective material properties based on the fractional combination of its constituent materials, the surrounding medium such as air, and the fluid collected. The lateral extent (e.g., length and width) of the local region affecting the thermal response is at least the lateral size of the heating element, increased in size in a manner similar to the probing depth of the measurement by the duration of time of heating and the effective thermal diffusivity of the fluid absorption and distribution layer 10.

The lateral size of a sensing device 100 is significantly larger than its vertical extent, meaning that the lateral size of the local region affecting the thermal response is much smaller than the lateral size of the sensing device 100. Constraints on minimum lateral size of a sensing device 100 include the required size of the antenna 120 in some embodiments, and the properties of the object emitting fluid where significant lateral surface area may be required to accurately sample the object. In one exemplary application, the object is a human skin and the fluid of interest is sweat, where typical surface area of a human is about 1.5 square meters to about 2 square meters, and a sampling area representative of human sweating patterns in a given region of the body may be on the order of 10 square centimeters, 100 square centimeters, or 500 square centimeters, where the desire would be to sample a population of at least hundreds or thousands of sweat glands across the sensing device 100. In another exemplary application, the object is a human wound and the fluid of interest is exudate, where a typical lateral dimension of a wound dressing may be about 5 centimeters up to about 30 centimeters or more. Achieving relatively uniform fluid distribution across the lateral dimensions of the fluid absorption and distribution layer 10 within a sensing device 100 is advantageous in these example applications and other envisioned fluid collection applications, such that a local region affecting the thermal response of the fluid absorption and distribution layer 10 can be measured and taken as representative of the state of the layer.

The sensing element (e.g., 136, 236, or 336) can have an effective sensing region 11 as shown in FIG. 1B. The local fluid concentration in the effective sensing region 11 can be determined, via the sensing element, by measuring the induced change in temperature ($\Delta T$). In some embodiments, the effective sensing region 11 may have a footprint dimension 11S that relates to the footprint of the sensing element on the layer 10. In some embodiments, the footprint dimension 11S may be comparable to the thickness D of the layer 10 between the opposite surfaces 12 and 14. In some embodiments, the layer 10 may have a thickness D in the range, for example, from about 0.5 mm to about 5 cm, from about 1 mm to about 2 cm, or from about 2 mm to about 1 cm. The layer 10 may have any surface area depending on desired applications. In many applications, the layer 10 may have a lateral dimension (e.g., length or width) at least 2 times, 5 times, or 10 times greater than the thickness D. In some embodiments, the sensing element may have an effective sensing footprint on the layer 10 (e.g., corresponding to the footprint dimension 11S in FIG. 1B) less than 20%, less than 10%, less than 5%, or less than 2% of the surface area of the layer 10.

The present disclosure provides fluid sensing devices based on heating a local region of a fluid absorption and distribution layer and measuring its thermal response. There is a desire to improve uniform distribution of fluid throughout the fluid absorption and distribution layer. Otherwise, the measurements can be susceptible to a non-uniform fluid distribution, which might be undesirable in some instances. For example, a non-uniform fluid distribution would require inclusion of a plurality of sensing elements to sufficiently map the non-uniformity in order to determine an accurate total fluid quantity, requiring additional materials cost and additional heating power and energy. One advantage of exemplary embodiments of the present disclosure is that a layer of fluid absorption and distribution material described herein can absorb fluid from an object to a first major surface thereof and uniformly distribute the absorbed fluid throughout the layer and to an opposite second major surface. With such a uniform fluid distribution, a sensing element with a relatively small footprint provided on the second major surface can measure a hydration level at a local area which is representative to the whole layer.

The layer 10 of fluid absorption and distribution material includes a porous fibrous nonwoven matrix. In some embodiments, the fluid absorption and distribution layer 10 may further include a plurality of particles of an amorphous, spheroidized metal silicate that are enmeshed in the porous fibrous nonwoven matrix.

Useful metal silicates include silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form (more preferably, amorphous, spheroidized metal silicates; most preferably, amorphous, spheroidized magnesium silicate). Metal silicates are known and can be chemically synthesized by known methods or obtained through the mining and processing of raw ores that are naturally-occurring.

In some embodiments, a fluid absorption and distribution layer can be prepared by essentially any process that can provide a fibrous nonwoven matrix (that is, a web or medium, other than a woven or knitted fabric, including interlaid fibers) having the particles enmeshed therein. Useful processes include meltblowing, spunbonding, and other air laying techniques; carding; wet laying; and the like; and combinations thereof (preferably, air laying, wet laying, and combinations thereof; more preferably, wet laying).

Fibers that are suitable for use in preparing the porous fibrous nonwoven matrix include pulpable fibers. Preferred pulpable fibers are those that are stable to radiation and/or to a variety of solvents. Useful fibers include polymeric fibers, inorganic fibers, and combinations thereof. Preferably, at least some of the fibers that are utilized exhibit a degree of hydrophilicity, and at least some of the fibers that are utilized exhibit a degree of hydrophobicity.

Suitable polymeric fibers include those made from natural (animal or vegetable) and/or synthetic polymers, including thermoplastic and solvent-dispersible polymers. Useful polymers include wool; silk; cellulosic polymers (for example, cellulose, cellulose derivatives, and the like); fluorinated polymers (for example, poly(vinyl fluoride), poly(vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; polyolefins (for example, poly(ethylene), poly(propylene), poly(1-butene), copolymers of ethylene and propylene, alpha olefin copolymers such as copolymers of ethylene or propylene with 1-butene, 1-hexene, 1-octene, and 1-decene, poly(ethylene-co-1-butene), poly(ethylene-co-1-butene-co-1-hexene), and the like); poly(isoprenes); poly(butadienes); polyamides (for example, nylon 6; nylon 6,6; nylon 6,12; poly(iminoadipoyliminohexamethylene); poly(iminoadipoyliminodecamethylene); polycaprolactam; and the like); polyimides (for example, poly(pyromellitimide) and the like); polyethers; poly(ether sulfones) (for example, poly(diphenylether sulfone), poly(diphenylsulfone-co-diphenylene oxide sulfone), and the like); poly(sulfones); poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl esters); poly(vinyl ethers); poly(vinyl alcohols); polyaramids (for example, para-aramids such as poly(paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); poly(carbonates); and the like; and combinations thereof. Preferred polymeric fibers include polyamides, polyolefins, polysulfones, and combinations thereof (more preferably, polyamides, polyolefins, and combinations thereof most preferably, nylons, poly(ethylene), and combinations thereof).

Suitable inorganic fibers include those that contain at least one inorganic material selected from glasses, ceramics, and combinations thereof. Useful inorganic fibers include fiberglasses (for example, E-glass, S-glass, and the like), ceramic fibers (for example, fibers made of metal oxides (such as alumina), silicon carbide, boron nitride, boron carbide, and the like), and the like, and combinations thereof. Useful ceramic fibers can be at least partially crystalline (exhibiting a discernible X-ray powder diffraction pattern or containing both crystalline and amorphous (glass) phases). Preferred inorganic fibers include fiberglasses and combinations thereof.

The fibers used to form the porous fibrous nonwoven matrix can be of a length and diameter that can provide a matrix having sufficient structural integrity and sufficient porosity for a particular application. For example, lengths of at least about 0.5 mm, 1 mm, 2 mm, 3 mm, 4 mm, 6 mm, 8 mm, 10 mm, 15 mm, or even 20 mm, (and combinations thereof), and diameters of at least about 10 microns (micrometer), 20 microns, or even 40 microns, (and combinations thereof) can be useful. Preferred fiber lengths and diameters will vary, depending upon factors including the nature of the fiber and the type of application. For example, fibrillated poly(ethylene) can be useful in lengths of about 1 mm to about 3 mm, and non-fibrillated nylon can be useful in lengths of about 6 mm to about 12.5 mm.

In some embodiments, to facilitate entrapment of the particles and/or to ensure a high surface area matrix, the fibers used to form the porous fibrous nonwoven matrix preferably include at least one fibrillated fiber (for example, in the form of a main fiber surrounded by many smaller attached fibrils). The main fiber generally can have a length in the range of about 0.5 mm to about 4 mm and a diameter of about 1 to about 20 micrometers. The fibrils typically can have a submicrometer diameter.

The porous fibrous nonwoven matrix can include two, three, four, or even more different types of fibers. For example, a nylon fiber can be added for strength and integrity, while fibrillated polyethylene can be added for entrapment of the particles. If fibrillated and non-fibrillated fibers are used, generally the weight ratio of fibrillated fibers to non-fibrillated fibers can be at least about 1:2, 1:1, 2:1, 3:1, 5:1, or even 8:1. Regardless of the type(s) of fibers chosen, the amount of fiber in the resulting absorption and distribution layer (in dry form) is preferably at least about 60 percent by weight up to about 100 percent by weight (based upon the total weight of all components of the absorption and distribution layer).

Preferably, the porous fibrous nonwoven matrix further includes at least one polymeric binder. Suitable polymeric binders include natural and synthetic polymeric materials that are relatively inert (exhibiting little or no chemical interaction with either the fibers or the particles). For some applications, polymeric resins, polymeric binders and combinations can be useful. Preferred polymeric binders include fibrous polymeric binders.

Suitable polymeric resins include, but are not limited to, natural rubbers, neoprene, styrene-butadiene copolymers, acrylate resins, polyvinyl chloride, polyvinyl acetate, and the like, and combinations thereof. Preferred polymeric resins include acrylate resins and combinations thereof. Suitable fibrous polymeric binders include adhesive-only type fibers (for example, Kodel™ 43UD fibers, available from Eastman Chemical Products, Kingsport, Tenn.), bicomponent fibers (for example, side-by-side forms such as Chisso ES polyolefin thermally bonded bicomponent fibers, available from Chisso Corporation, Osaka, Japan; sheath-core forms such as Melty™ Fiber Type 4080 bicomponent fibers having a polyester core and a polyethylene sheath, available from Unitika Ltd., Osaka, Japan; and the like), and the like, and combinations thereof. Preferred fibrous polymeric binders include bicomponent fibers and combinations thereof (more preferably, sheath-core bicomponent fibers and combinations thereof).

Regardless of the type of polymeric binder used, the amount of binder in the resulting absorption and distribution layer (in dry form) generally can be from about 5 weight percent to about 15 weight percent (preferably, about 9-13 weight percent), based upon the total weight of all components of the absorption and distribution layer. Such amounts of polymeric binder generally can provide the porous fibrous nonwoven matrix with sufficient integrity for use in many applications, while not significantly coating the particles.

In some embodiments, the fluid absorption and distribution layer 10 can be prepared by a process include (a) providing a plurality of the above-described fibers; (b) providing a plurality of the above-described particles; and (c) forming at least a portion of the plurality of fibers into a porous fibrous nonwoven matrix having at least a portion of the plurality of particles enmeshed therein. As mentioned above, the forming can be carried out by essentially any process that can provide a fibrous nonwoven matrix (that is, a web or medium, other than a woven or knitted fabric, including interlaid fibers) having the particles enmeshed therein. Useful processes include meltblowing, spunbonding, and other air laying techniques; carding; wet laying; and the like; and combinations thereof (preferably, air laying, wet laying, and combinations thereof; more preferably, wet laying).

Preferably, the forming is carried out by using a wet laying or "wet-laid" process including (a) forming a dispersion including the plurality of fibers, the plurality of particles (which can be added and dispersed along with the other components prior to carrying out other process steps or, if desired, can be added and dispersed later in the process but generally prior to removal of dispersing liquid), and at least one fibrous polymeric binder in at least one dispersing liquid (preferably, water); and (b) removing the dispersing liquid from the dispersion. In such a process, the fibers can be dispersed in the dispersing liquid to form a slurry. If desired, the fibers can include additives or chemical groups or moieties to assist in their dispersion. For example, polyolefin-based fibers can include maleic anhydride or succinic anhydride functionality, or, during the melt-processing of polyethylene fibers, a suitable surfactant can be added.

When fibrous polymeric binders are used as the polymeric binder, dewatering can generally be carried out first, followed by heating to finish the dewatering and to melt the fibrous polymeric binders (and thereby deposit polymeric binder on the fibers).

The following description is based on a hand-sheet method, although those skilled in the art can readily recognize how to adapt such a method to provide for a continuous process. In a preferred wet-laid process, the fibers can be blended in a container in the presence of the dispersing liquid (for example, water, a water-miscible organic solvent such as an alcohol, or a combination thereof). The amount of shear used to blend the resulting mixture has not been found to affect the ultimate properties of the resulting absorption and distribution layer, although the amount of shear introduced during blending is preferably relatively high. Thereafter the particles can be added to the container.

The resulting fiber-liquid slurry, can be poured into a mold, the bottom of which can be covered by a screen. The dispersing liquid (preferably, water) can be allowed to drain from the mixture (in the form of a wet sheet) through the screen. The fibers get deposited onto the porous screen while allowing the dispersing liquid to drain (by gravity or by vacuum). After sufficient liquid has drained from the sheet, the wet sheet generally can be removed from the mold and dried by pressing, heating, or a combination of the two. Generally, pressures of about 300 to about 600 kPa and temperatures of about 100 to about 200° C. (preferably, about 100 to about 130° C.) can be used in these drying processes. When fibrous polymeric binders are used as the polymeric binder in the preferred wet-laid process, the applied heat can be used to melt the fibrous polymeric binders.

The resulting dry sheet can have an average thickness of at least about 1, 2, 4, or even 5 mm. The resulting dry sheet has a pattern on the side that faces the forming screen.

As mentioned above, the particles can be microparticles. The microparticles can be entrapped in the porous fibrous nonwoven matrix through either chemical interactions (for example, chemical bonding) or physical interactions (for example, adsorption or mechanical entrapment), depending upon the nature of the fibers that are utilized. Preferred embodiments of the absorption and distribution layer include those including at least one fibrillated fiber that can affect mechanical entrapment of the particles.

The amount of particles in the absorption and distribution layer preferably can be at least about 20, 30, or even 40 weight percent (based upon the total weight of all components of the absorption and distribution layer). The particles are entrapped in the porous fibrous nonwoven matrix and preferably distributed within it (more preferably, the particles are distributed essentially uniformly throughout the matrix).

The basis weight of the absorption and distribution layer (in the form of sheet material) can be in the range of about 150 to about 500 g/m² (preferably, in the range of about 170 to about 400 g/m²; more preferably, about 180 to about 380 g/m²).

Generally, the average pore size of the sheet material can be in the range of about 0.1 to about 10 micrometers, as measured by scanning electron microscopy (SEM). Void volumes in the range of about 20 to about 80 volume percent can be useful (preferably, about 40 to about 60 volume percent). The porosity of the sheet materials can be modified (increased) by including fibers of larger diameter or stiffness in the fiber mixture.

The uncalendared sheet material can be cut to a desired size and used to carry out the fluid absorption and distribution process of the present disclosure. A single layer of sheet material can be effective in carrying out the fluid absorption and distribution process of the present disclosure.

While not wanting to be bound by theory, we believe a technical advantage of using a wet laying or wet-laid process to make the layer of fluid absorption and distribution material is the ability to use fibers with a varying degree of hydrophilicity and hydrophobicity that provides tortuous paths for the fluid to travel through the layer. Such a fibrous nonwoven matrix was found to effectively distribute fluid in a single layer without the need to create separate fluid absorption and distribution layers. In addition, the random fibrous arrangement allows fluid distribution which further allows effective sensing measurements unlike quick wicking, open cell material.

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Exemplary embodiments of the present disclosure may take on various modifications and alterations without departing from the spirit and scope of the present disclosure.

Accordingly, it is to be understood that the embodiments of the present disclosure are not to be limited to the following described exemplary embodiments, but is to be controlled by the limitations set forth in the claims and any equivalents thereof.

LISTING OF EXEMPLARY EMBODIMENTS

Exemplary embodiments are listed below. It is to be understood that any one of embodiments 1-14 and 15-21 can be combined.

Embodiment 1 is a fluid sensing device comprising:
  one or more hydration sensors; and
  a layer of fluid absorption and distribution material,
  wherein the one or more hydration sensors is disposed on the layer of fluid absorption and distribution material, and
  wherein the layer of fluid absorption and distribution material comprises a porous fibrous nonwoven matrix.

Embodiment 2 is the fluid sensing device of embodiment 1, wherein the porous fibrous nonwoven matrix comprises at least one fibrillated fiber.

Embodiment 3 is the fluid sensing device of embodiment 1 or 2, wherein the fibers of said porous fibrous nonwoven matrix are selected from polymer fibers, inorganic fibers, and combinations thereof.

Embodiment 4 is the fluid sensing device of embodiment 3, wherein the polymer fibers comprise at least one polymer selected from polyamides, polyolefins, and combinations thereof.

Embodiment 5 is the fluid sensing device of embodiment 3 or 4, wherein inorganic fibers comprise at least one inorganic material selected from glasses, ceramics, and combinations thereof.

Embodiment 6 is the fluid sensing device of any one of embodiments 1-5, wherein the porous fibrous nonwoven matrix comprises at least one polymeric binder.

Embodiment 7 is the fluid sensing device of embodiment 6, wherein the polymeric binder includes one or more fibrous polymeric binders.

Embodiment 8 is the fluid sensing device of any one of embodiments 1-7 wherein the layer of fluid absorption and distribution material further comprises a plurality of particles of an amorphous, spheroidized metal silicate, wherein the particles are enmeshed in the porous fibrous nonwoven matrix.

Embodiment 9 is the fluid sensing device of any one of embodiments 1-8, wherein a first major surface of the layer has a patterned or textured surface.

Embodiment 10 is the fluid sensing device of any one of embodiments 1-9 further comprising an antenna, and the one or more hydration sensors including an RF component electrically coupled to the antenna.

Embodiment 11 is the fluid sensing device of embodiment 10, wherein the one or more hydration sensors further comprises a thermal source element electrically coupled to the RF element to change a thermal condition of a target area.

Embodiment 12 is the fluid sensing device of embodiment 11, wherein the one or more hydration sensors further comprise a temperature sensing element thermally coupled to the thermal source element to sense a temperature of the thermal source.

Embodiment 13 is the fluid sensing device of any one of embodiments 1-12, wherein the one or more hydration sensors are configured to measure a hydration level of an object when the one or more hydration sensors along with the layer of fluid absorption and distribution material is disposed proximate to the object.

Embodiment 14 is the fluid sensing device of any one of embodiments 1-13, wherein the one or more hydration sensors has an effective sensing footprint on the layer less than 10% of the surface area of the layer.

Embodiment 15 is a method for quantitative fluid sensing comprising:
  providing a layer of fluid absorption and distribution material having a first major surface in fluid communication with an object;
  absorbing fluid from the object to the first major surface of the layer and laterally distributing the absorbed fluid throughout the layer and to a second major surface of the layer opposite the first major surface; and
  providing one or more hydration sensors disposed on the second major surface of the layer to measure a hydration level thereof,
  wherein the layer of fluid absorption and distribution material comprises a porous fibrous nonwoven matrix.

Embodiment 16 is the method of embodiment 15, wherein providing the layer of fluid absorption and distribution material comprises forming the layer by a wet-laid process.

Embodiment 17 is the method of embodiment 16, wherein the wet-laid process comprises forming a dispersion comprising a plurality of fibers, optionally a plurality of particles of an amorphous, spheroidized metal silicate, dispersed in a dispersing liquid.

Embodiment 18 is the method of embodiment 17, wherein the wet-laid process further comprises dispersing and depositing a fibrous polymeric binder onto the plurality of fibers.

Embodiment 19 is the method of embodiment 17 or 18, further comprising removing the dispersing liquid from the dispersion to form a wet sheet, wherein the dispersion is provided onto a screen which allows the dispersing liquid to drain therethrough.

Embodiment 20 is the method of embodiment 19, further comprising drying the web sheet to form a patterned surface on the side that was in contact with the screen.

Embodiment 21 is the method of any one of embodiments 15-20, wherein the hydration sensors have an effective sensing footprint on the layer less than 10% of the surface area of the layer.

EXAMPLES

These examples are merely for illustrative purposes and are not meant to be limiting on the scope of the appended claims. All parts, percentages, ratios, etc. in the examples and the rest of the specification are by weight, unless noted otherwise.

Summary of Materials

Unless otherwise noted, all parts, percentages, ratios, etc. in the Examples and the rest of the specification are by weight. Table 1 provides abbreviations and a source for all materials used in the Examples below:

TABLE 1

| Abbreviation | Description and Source |
|---|---|
| CM-111 | Amorphous, spheroidized magnesium silicate purchased from 3M Company as 3M Cosmetic Microspheres |
| Fiber 1 | 1.2 mm polyethylene fibers, obtained from Minifibers, Inc., Johnson City, TN, under the trade designation "FYBREL |

TABLE 1-continued

| Abbreviation | Description and Source |
|---|---|
| | E620" |
| Fiber 2 | 0.8-1.1 mm fibrillated high density polyethylene fibers, obtained from Minifibers, Inc., Johnson City, TN, under the trade designation "SHORT STUFF ® Polyethylene grade E505" |
| Fiber 3 | 6 denier ¼ inches long chopped nylon fibers, obtained from Minifibers, Inc, Johnson City, TN. |
| Fiber 4 | 6 denier ½ inches long chopped nylon fibers, obtained from Minifibers, Inc., Johnson City, TN |
| Fiber 5 | 1 denier bicomponent ethylene vinyl acetate/polypropylene fibers, obtained from Minifibers, Inc., Johnson City, TN |
| Fiber 6 | long glass fibers, obtained from Johns Manville, Denver, CO, under the trade designation "MICRO-STRAND 106-475" |
| Fiber 7 | 2 denier bicomponent polyester/polyester fibers, obtained from Minifibers, Inc., Johnson City, TN |

EXAMPLES

Examples E1-E4 of fluid absorption and distribution materials were prepared by mixing various amounts of fibers as shown in Table 2 below. All fibers were added to 3 liters of cold deionized water in a 4 L blender (available from VWR, Radnor, PA, under the trade designation "WARING COMMERCIAL HEAVY DUTY BLENDER, MODEL 37BL84"). Mixtures of Examples E1 and E3 were blended at medium speed for 60 seconds. The mixture was examined for uniform dispersion of the fibers without nits or clumps. A fourth liter of water was added and the mixture was blended further for 30 seconds on medium speed to break up clumps. Mixture of Example E2 was blended at low speed for 30 seconds. The mixture was examined for uniform dispersion of the fibers without nits or clumps. A fourth liter of water was added and the mixture was blended further for 15 seconds on low speed to break up clumps.

A felt was prepared using a pad maker apparatus (obtained from Williams Apparatus, Watertown, NY, under the trade designation "TAPPI") that had a box measuring about 30 centimeters (12 inches) square and 30 centimeters (12 inches) high with a fine mesh screen at the bottom and a drain valve. The box was filled with tap water up to a height of about 1 centimeter above the screen. On the screen, a 14-inch×12-inch piece of a polyethylene spunbond (PET Lutradur 7240 obtained from Fiberweb, Cincinnati, Ohio) was laid as scrim on the screen. Each fiber mixture was poured into the box and the valve was opened immediately which created a vacuum that pulled the water out of the box.

The wet-laid felt was transferred from the apparatus onto a 20-centimeter square sheet of blotter paper (96-pound white paper, obtained from Anchor Paper, St. Paul, MN). The felt was sandwiched between 2 to 4 layers of blotter paper, to blot excess water. The pressed felt was then transferred onto a fresh sheet of blotter paper and placed in an oven (Thermo Scientific HERATherm OMS100 series, purchased from VWR International) set at 110° C. for about 3.5 hours to remove residual water and to form a porous wet-laid matrix. Felts of Examples E1 and E3 were dried at 125° C. for about 4 hours. Felt of Example E2 was dried at 110° C. for about 3.5 hours. Example E4 was made, following basic process described above, in an approximately 350-gallon batch on pilot scale wet-laying equipment. The 350 gsm (grams per square meter) was dried at 110° C.

TABLE 2

| Material (grams) | Example E1 | Example E2 | Example E3 | Example E4 |
|---|---|---|---|---|
| Fiber 1 | 0.00 | 0.00 | 0.00 | 3923.57 |
| Fiber 2 | 22.23 | 16.80 | 11.13 | 0.00 |
| Fiber 3 | 6.00 | 0.00 | 3.00 | 371.94 |
| Fiber 4 | 0.00 | 4.5 | 0.00 | 54.53 |
| Fiber 5 | 0.00 | 3.38 | 0.00 | 322.05 |
| Fiber 6 | 3.50 | 2.66 | 1.75 | 249.47 |
| Fiber 7 | 4.50 | 0.00 | 2.25 | 0.00 |
| Additive (gms) | 0.0 | 0.0 | 0.0 | 1020.58 |
| Basis Weight in grams per square meter | 377 | 284 | 184 | 350 |

Comparative Example C1

Comparative Example C1 is an absorbent open-cell polyurethane foam from 3M Company (St. Paul, MN) under the trade designation MSX-6916B 3M Absorbent Polyurethane Foam.

Optical Surface Images

Figure 2B:
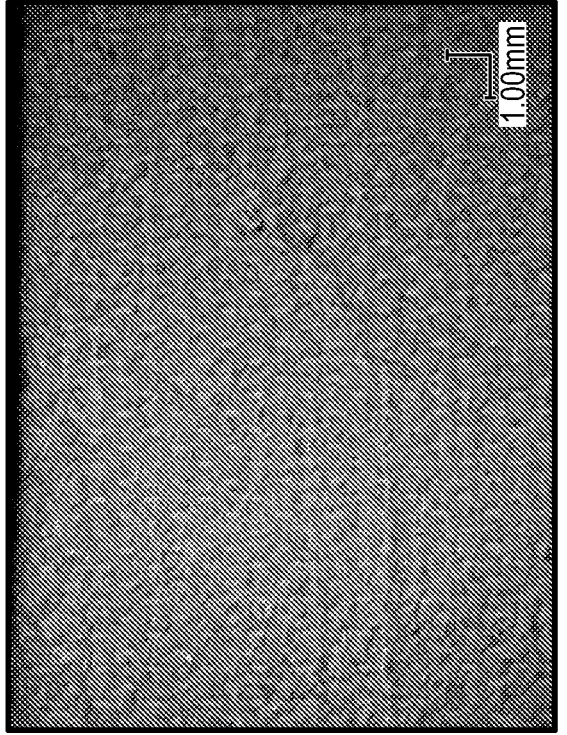
FIG. 2B illustrates an optical image of another major surface of Example E4.
Figure 2A:
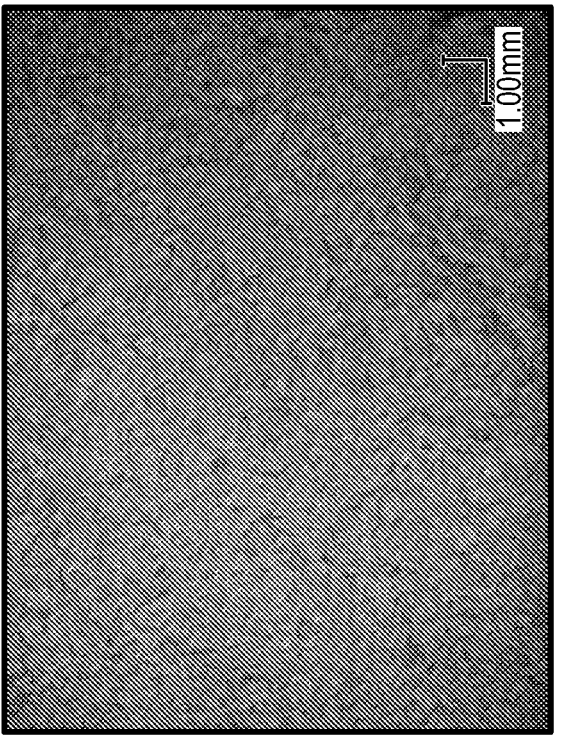
FIG. 2A illustrates an optical image of one major surface of Example E4.
Figure 3B:
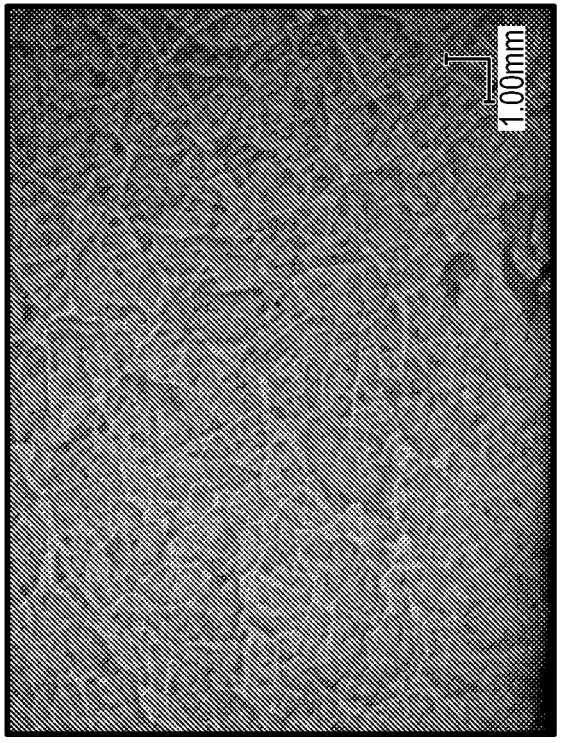
FIG. 3B illustrates an optical image of another major surface of Example E1.
Figure 3A:
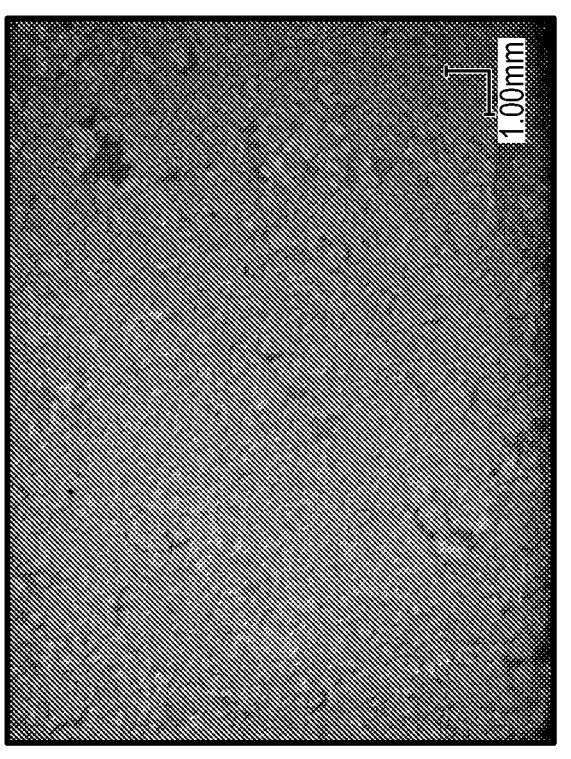
FIG. 3A illustrates an optical image of one major surface of Example E1.
Figure 4B:
FIG. 4B illustrates an optical image of another major surface of Comparative Example C1.
Figure 4A:
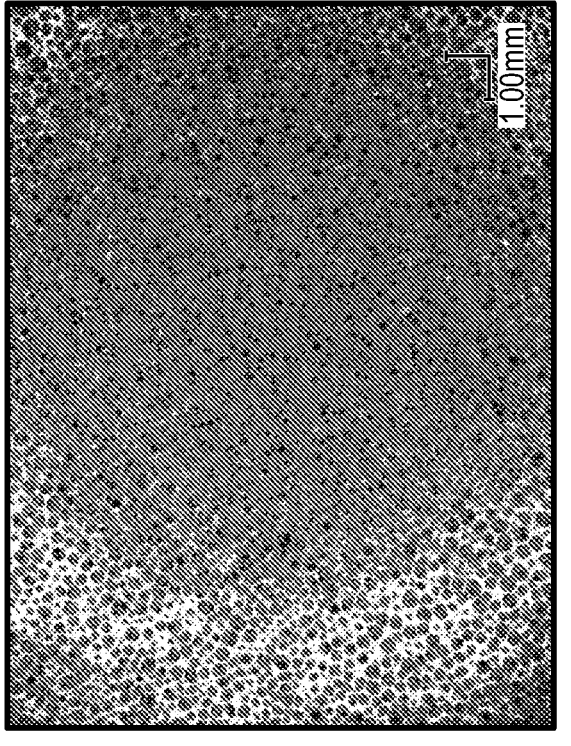
FIG. 4A illustrates an optical image of one major surface of Comparative Example C1.

Reflected-light microscope images were obtained for each major surface of Examples E4 and E1 and Comparative Example C1, as shown in FIGS. 2A-B, 3A-B and 4A-B, respectively. The texture visible for Example E4 as shown in FIG. 2B is produced by the screen employed in the wet-laid process as the substrate for the web during formation. The other surface of Example E4, as shown in FIG. 2A, has a random texture. The porosity of this material E4 is not visible from either surface. The surfaces of Example E1 in FIGS. 3A-B each have a random texture, and similar to E4 the material porosity is not visible from either surface. The surfaces of Comparative Example C1 in FIGS. 4A-B are smoother, especially as shown in FIG. 4A where a specular reflection from the microscope light ring is visible, and the material C1 is visibly porous into the material volume with relatively circular pore shapes.

Since all the samples shown in FIGS. 2A-4B are predominantly white in color with minimal contrast present, the contrast of each image was digitally enhanced by reducing the image level range from 0-255 levels (i.e. 8-bit grayscale) down to 150-255 levels. The scale bar in the lower-right corner of each image shows a 1.00 mm length for reference.

Fluid Absorption and Distribution Tests

The set of experiments described below involve "point source" input of a controlled amount of fluid into a fluid absorption and distribution material sample at one location, and measurement of the quantity of fluid present at two locations on the opposite surface of the fluid absorption and distribution material. This setup gives quantitative measures of local fluid concentration and lateral fluid spreading through the volume of each fluid absorption and distribution material. Local fluid concentration at a given sensor location is measured by introducing a known amount of heat into a material and measuring the resulting temperature change with time, where local fluid concentration is inversely proportional to the induced change in temperature ($\Delta T$) per unit of input power. Lateral fluid spreading is calculated by comparing the sensed local fluid concentrations among two spatial locations.

Test Setup

A test assembly was provided with a reservoir of fluid, 2 ports for attachment to syringe pump and air purge, a small central port out of the top surface of the reservoir for delivery of fluid into the fluid absorption and distribution material under test. A polycarbonate film spacer rests on top of the top surface of the reservoir to improve the accuracy of fluid delivery into the sample, reducing self-wicking of additional fluid from the reservoir.

Tips of two nominally identical sensor tails for sensing of local fluid quantity were provided on a 1-inch square sample of fluid absorption and distribution material. The sensor tails were designed with a small surface-mount thin-film resistor (1 kΩ, 0201-size 0.6×0.3×0.23 mm, Susumu) and a small surface-mount thermistor (100 kΩ at 25° C. 0201-size 0.6×0.3×0.3 mm, Panasonic) in close proximity to one another, to enable measurement of heat transfer by a modified transient plane source method. At a time t0, a constant amount of power is input to the resistor (typically 1 mW or 2 mW), and the resistance of the thermistor is sampled periodically to obtain a profile of temperature versus time. The resulting temperature change from t0 to the end of the measurement is proportional to the thermal conductivity of the surrounding environment, which in this setup is proportional to the fraction of fluid contained in a local region of the fluid absorption and distribution material. The sensor tail substrates used DuPont LF8520 copper-laminated polyimide (0.0007" copper, 0.001" acrylic adhesive, and 0.002" polyimide) with a DuPont LF0110 Coverlay layer (0.001" polyimide and 0.001" acrylic adhesive); four traces each with 0.100 mm trace width were etched to make electrical connection to the component pads, and the components were attached to the pads by soldering.

A layer of Parafilm-M was added to cover the sensing circuit to provide a moisture barrier; a layer of MSX-6916B absorbent polyurethane foam (3M Company, St. Paul, MN) added for thermal isolation; and a mass added to maintain thermal contact between the sensor tips and the fluid absorption and distribution material.

Test Samples

One-inch square samples of each fluid absorption and distribution materials of Examples E1-E4 and Comparative Example C1 were cut from a sheet of material, and two sensors were placed in contact with the top surface at a center and an "edge" location as depicted in the figure. The edge location was approximately 1 to 1.5 cm from the center location, along the diagonal of the square sample.

Several sample sets were prepared, with properties of each sample summarized in the following table. Each thickness was measured with a ratcheting micrometer (Mitutoyo model 293-344) modified to provide even pressure on each major surface of a sample by 2 attached square polycarbonate plates with 2.5 cm edge dimension.

TABLE 3

| Sample set ID | Materials | N replicates tested | Thicknesses (mm) | Dry masses (g) |
|---|---|---|---|---|
| S1 | E1 | 5 | 2.4 | 0.25 |
| | | | 3.3 | 0.36 |
| | | | 2.4 | 0.25 |
| | | | 2.7 | 0.28 |
| | | | 2.6 | 0.31 |
| S2 | E2 | 5 | 2.6 | 0.23 |
| | | | 2.4 | 0.21 |
| | | | 2.6 | 0.22 |
| | | | 2.1 | 0.22 |
| | | | 2.3 | 0.21 |
| S3 | E3 | 4 | 1.3 | 0.13 |
| | | | 1.5 | 0.18 |
| | | | 1.6 | 0.17 |
| | | | 1.5 | 0.18 |
| S4-1 | E4 | 3 "Patterned" (with textured | 1.4 | 0.23 |
| | | | 1.5 | 0.21 |

TABLE 3-continued

| Sample set ID | Materials | N replicates tested | Thicknesses (mm) | Dry masses (g) |
|---|---|---|---|---|
| | | surface facing the fluid delivery) | 1.4 | 0.23 |
| S4-2 | E4 | 3 "Reversed" (with textured | 1.4 | 0.22 |
| | | | 1.7 | 0.22 |
| | | surface facing the sensors) | 1.5 | 0.22 |
| SC1 | C1 | 1 | 2.4 | 0.16 |

Test Results

Figure 5A:
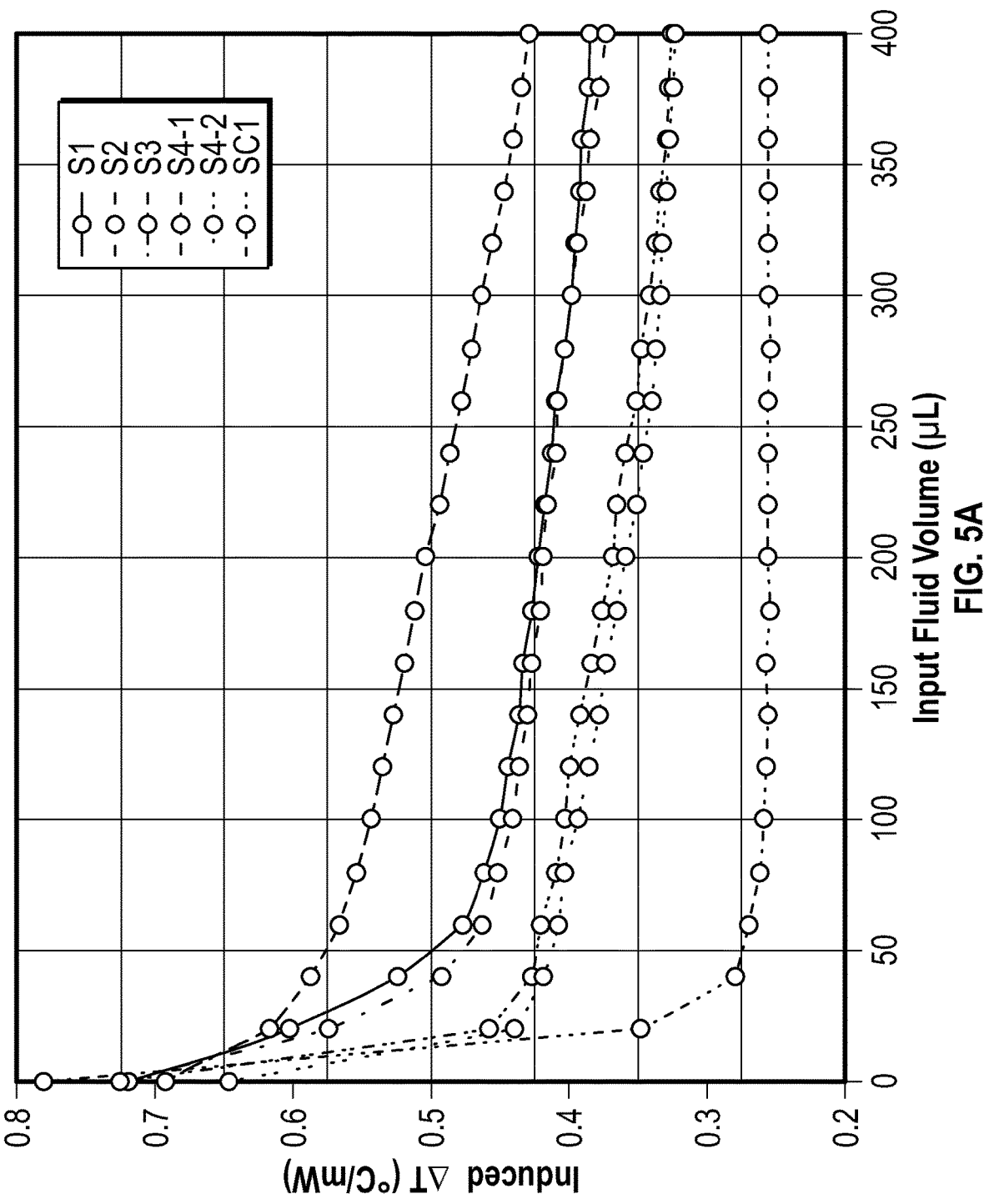
FIG. 5A illustrates plots of induced temperature change versus fluid volume for Examples and Comparative Example(s).
Figure 5B:
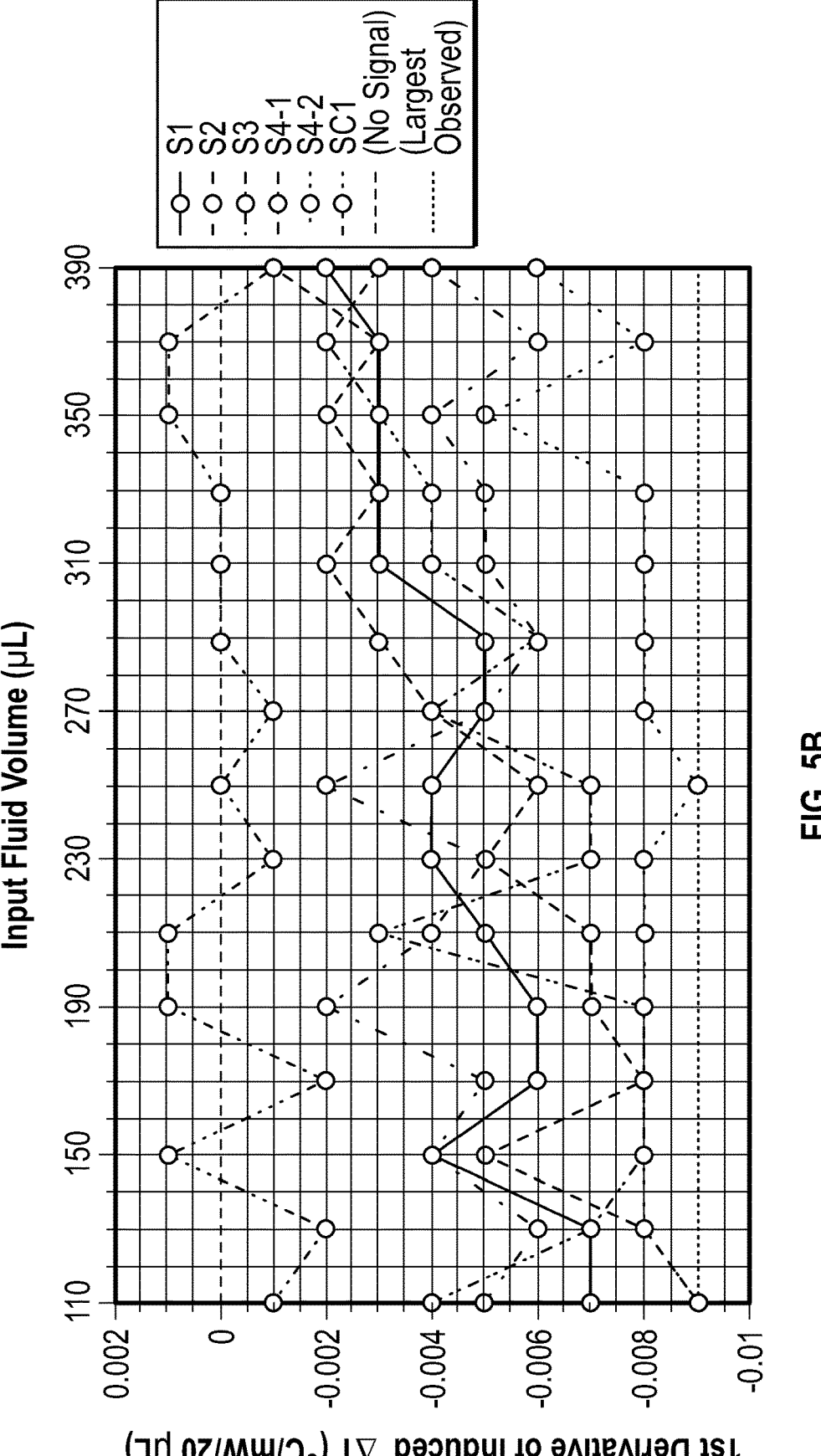
FIG. 5B illustrates plots of $1^{st}$ derivative of the induced temperature change of FIG. 5A versus fluid volume.
Figure 6:
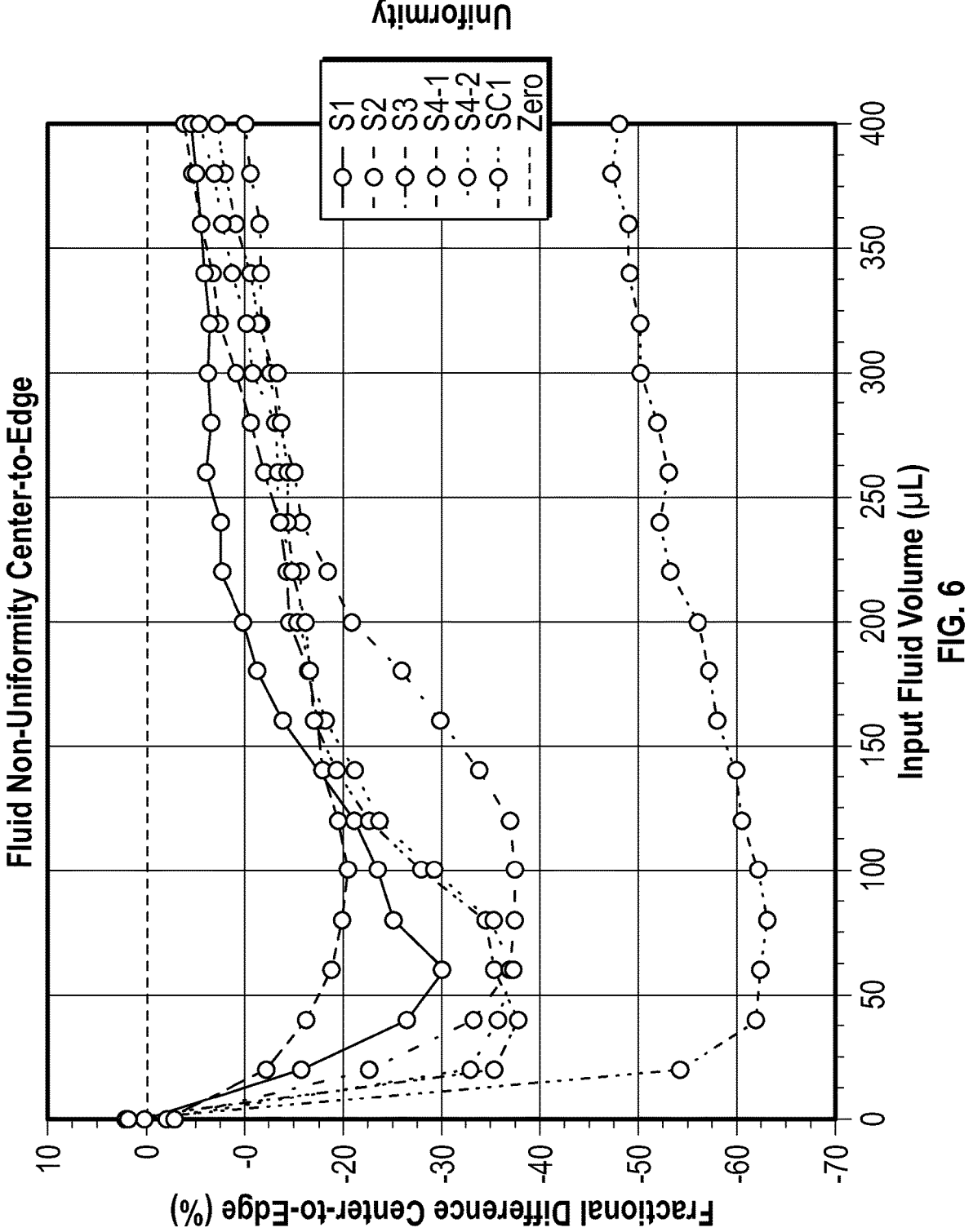
FIG. 6 illustrates plots of fluid distribution uniformity versus fluid volume for Examples and Comparative Example(s).

For controlled fluid injection at the Center sensor location, the averaged sensor readings at the Center sensor location and the Edge sensor location for all 6 sample sets is shown in FIGS. 5A-B and 6, each described in turn below.

With results measured at the Center sensor location shown in FIG. 5A, it can be seen that the sample set SC1 almost immediately saturates with very little fluid input, despite its relatively large thickness. Significant signal drops in the initial 20 µL are also seen in the sample set S4-2 and the sample set S3. The sample sets S1 and S2 each have a response becoming more linear across the full range of fluid injection, and the best performance for quantitative fluid sensing within these sets is seen in the sample set S4-1 which is relatively linear across the range of fluid input, with a relatively large and consistent incremental signal change for each fluid increment, and showing very little saturation even after 400 µL of injection. This behavior indicates the fluid is consistently being spread laterally rather than accumulating within the local region near the fluid injection site.

The qualitative description above of each material's "linearity", "incremental signal change", and "saturation" performance can be quantified by looking at the numerical first derivative of each of the above induced ΔT curves. An ideal linear material will have a constant first derivative for all fluid volumes, and saturation occurs when the first derivative becomes effectively zero. These discrete first derivatives are shown in FIG. 5B, omitting the initial 100 µL or so where all materials respond rather strongly to fluid.

Metrics obtained from the first derivatives of FIG. 5B that correspond to the qualitative descriptions are shown in the following Table 4. The desire for a consistently large "incremental signal change" is represented by the median of the derivative curve; the desire for high linearity (low non-linearity) is represented by the range of the derivative with range defined as the difference between its maximum point and minimum point; the desire to avoid saturation is represented by the value of the derivative at the final fluid injection data point. The sample set S4-1 exhibited the best performance for all metrics.

TABLE 4

| Sample set | Incremental signal change: Median $\|d(\Delta T)\|$ (° C./mW/20 µL) | Non-linearity: Range = max. $\|d(\Delta T)\|$ − min. $\|d(\Delta T)\|$ (° C./mW/20 µL) | Saturation: $\|d(\Delta T)\|$ at end (° C./mW/20 µL) |
|---|---|---|---|
| S1 | 0.005 | 0.114 | 0.002 |
| S2 | 0.005 | 0.150 | 0.004 |
| S3 | 0.006 | 0.266 | 0.003 |
| S4-1 | 0.008 | 0.069 | 0.006 |
| S4-2 | 0.006 | 0.206 | 0.001 |
| SC1 | 0.001 | 0.431 | <0.001 |

The measurement data from the Center location and the Edge sensor location from the same set of experiments were compared. To reiterate, fluid injection occurs at the Center location, so qualitatively here we see a delay in the onset of noticeable changes followed by gradual reduction in the sensor signal. Going further, one quantitative measure of non-uniformity of fluid distribution in each material is the fractional difference between the sensor signal at the Edge location relative to the respective signal at the Center location. The resulting curve for each such non-uniformity calculation is shown in FIG. 6. The fractional change calculation was done on a sample-by-sample basis, and the resulting fractional changes are then averaged to provide a mean fractional difference for each sample set. Also, the fractional change calculation was done on inverse $\Delta T$ as follows:

$$\frac{\frac{1}{\Delta T_{Edge}} - \frac{1}{\Delta T_{Center}}}{\frac{1}{\Delta T_{Center}}} \cdot 100\%$$

Inverse $\Delta T$ was utilized in these fractional calculations to avoid potential numerical issues as induced $\Delta T$ would approach zero for large fluid quantity and small thermal interface resistance between the sensor and the fluid absorption and distribution material.

In the data above, the smallest peak non-uniformity is found in the sample set S4-1. The sample set SC1 has the worst non-uniformity at all input fluid volumes. The sample set S1 has the smallest non-uniformity at some of the input fluid volumes, but the uniformity is less consistent across the range of fluid volume and the fluid distribution is less uniform than sample set S4-1 at the smaller fluid volumes.

This non-uniformity can be further quantified from these curves into scalars by recording the peak non-uniformity of each curve, and the area enclosed by each curve and a horizontal line at zero, as reported in the following table 5:

TABLE 5

| Sample set | Peak non-uniformity % | Area enclosed (µL) |
| --- | --- | --- |
| S1 | −30 | −51 |
| S2 | −37 | −88 |
| S3 | −38 | −75 |
| S4-1 | −20 | −52 |
| S4-2 | −37 | −74 |
| SC1 | −63 | −215 |

The samples with the most favorable fluid distribution performance in each category again show sample set S4-1 as the best and sample set S1 next best. The area enclosed was calculated by a numerical integration (by trapezoidal method) of each 'fractional difference center-to-edge' curve above (not scaled by 100 to units of %), which yields a single number for each sample set to quantify its overall non-uniformity, in units of fluid volume. For reference, a sample with −100% non-uniformity (−1.00 fractional units) for all fluid volumes would give a −400 µL area enclosed, and a sample with −50% non-uniformity (−0.50 fractional units) for all fluid volumes would give a −200 µL area enclosed.

Reference throughout this specification to "one embodiment," "certain embodiments," "one or more embodiments," or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments. While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about." Furthermore, various exemplary embodiments have been described. These and other embodiments are within the scope of the following claims.

What is claimed is:

1. A fluid sensing device comprising:

one or more hydration sensors;

a layer of fluid absorption and distribution material, the layer of fluid absorption and distribution material comprising a porous fibrous nonwoven matrix, wherein the one or more hydration sensors is disposed on the layer of fluid absorption and distribution material; and a thermal heating element that is in thermal contact with a target area of the layer of fluid absorption and distribution material, the heating element being configured to introduce a known amount of heat to the target area of the layer of fluid absorption and distribution material, wherein the one or more hydration sensors are configured to determine a quantity of fluid absorbed by the layer of fluid absorption and distribution material based on a thermal response of the layer of fluid absorption and distribution material to the known amount of heat introduced to the target area of the layer of fluid absorption and distribution material by the thermal heating element.

2. The fluid sensing device of claim 1, wherein the porous fibrous nonwoven matrix comprises at least one fibrillated fiber.

3. The fluid sensing device of claim 1, wherein the porous fibrous nonwoven matrix comprises fibers selected from polymer fibers, inorganic fibers, and combinations thereof.

4. The fluid sensing device of claim 3, wherein the polymer fibers comprise at least one polymer selected from polyamides, polyolefins, and combinations thereof.

5. The fluid sensing device of claim 1, wherein the porous fibrous nonwoven matrix comprises at least one polymeric binder.

6. The fluid sensing device of claim 5, wherein the polymeric binder includes one or more fibrous polymeric binders.

7. The fluid sensing device of claim 1 wherein the layer of fluid absorption and distribution material further comprises a plurality of particles of an amorphous, spheroidized metal silicate, wherein the particles are enmeshed in the porous fibrous nonwoven matrix.

8. The fluid sensing device of claim 1, wherein a first major surface of the layer has a patterned or textured surface.

9. The fluid sensing device of claim 1 further comprising an antenna, and the one or more hydration sensors including an RF component electrically coupled to the antenna.

10. The fluid sensing device of claim 1, wherein the one or more hydration sensors are configured to measure a hydration level of an object when the one or more hydration sensors along with the layer of fluid absorption and distribution material is disposed proximate to the object.

11. The fluid sensing device of claim 1, wherein the one or more hydration sensors has an effective sensing footprint on the layer less than 10% of the surface area of the layer.

12. A method for quantitative fluid sensing, the method comprising:

providing a layer of fluid absorption and distribution material having a first major surface in fluid communication with an object, the layer of fluid absorption and distribution material comprising a porous fibrous nonwoven matrix;

absorbing fluid from the object to the first major surface of the layer and laterally distributing the absorbed fluid throughout the layer and to a second major surface of the layer opposite the first major surface;

providing one or more hydration sensors disposed on the second major surface of the layer to measure a hydration level thereof; and providing a thermal heating element that is in thermal contact with a target area of the layer of fluid absorption and distribution material, the heating element being configured to introduce a known amount of heat to the target area of the layer of fluid absorption and distribution material, wherein the one or more hydration sensors are configured to determine a quantity of fluid absorbed by the layer of fluid absorption and distribution material based on a thermal response of the layer of fluid absorption and distribution material to the known amount of heat introduced to the target area of the layer of fluid absorption and distribution material by the thermal heating element.

13. The method of claim 12, wherein providing the layer of fluid absorption and distribution material comprises forming the layer by a wet-laid process.

14. The method of claim 13, wherein the wet-laid process comprises forming a dispersion comprising a plurality of fibers, and a plurality of particles of an amorphous, spheroidized metal silicate, dispersed in a dispersing liquid.

15. The method of claim 14, wherein the wet-laid process further comprises dispersing and depositing a fibrous polymeric binder onto the plurality of fibers.

16. The method of claim 14, further comprising removing the dispersing liquid from the dispersion to form a wet sheet, wherein the dispersion is provided onto a screen which allows the dispersing liquid to drain therethrough.

17. The method of claim 16, further comprising drying the web sheet to form a patterned surface on the side that was in contact with the screen.

\* \* \* \* \*